United States Patent [19]

Bruno

[11] Patent Number: 4,962,275

[45] Date of Patent: Oct. 9, 1990

[54] METHOD AND APPARATUS FOR SUPERCRITICAL FLUID EXTRACTION SOLUTION SEPARATION

[75] Inventor: Thomas J. Bruno, Broomfield, Colo.

[73] Assignee: United States of America as represented by the Secretary of Commerce, Washington, D.C.

[21] Appl. No.: 482,589

[22] Filed: Feb. 21, 1990

[51] Int. Cl.[5] ............................................. C07C 7/10
[52] U.S. Cl. .................................. 585/834; 585/835; 585/866; 210/634; 426/490
[58] Field of Search ....................... 585/834, 835, 866; 210/511, 519, 634, 800, 801, 804; 426/422, 424, 425, 490

[56] References Cited

U.S. PATENT DOCUMENTS

| | | | |
|---|---|---|---|
| 2,432,021 | 12/1947 | Larner | 585/834 X |
| 2,741,643 | 4/1956 | Jones et al. | 585/834 X |
| 3,356,753 | 12/1967 | Sarnecki | 585/866 X |
| 3,939,281 | 2/1976 | Schwengers | 426/425 |
| 3,966,981 | 6/1976 | Schultz | 426/425 |
| 4,123,559 | 10/1978 | Vitzthum et al. | 426/312 |
| 4,198,432 | 4/1980 | Vitzthum et al. | 426/312 |
| 4,212,895 | 7/1980 | Laws et al. | 426/429 |
| 4,218,491 | 8/1980 | Laws et al. | 426/429 |
| 4,250,331 | 2/1981 | Shimshick | 562/485 |
| 4,282,259 | 8/1981 | Wheldon et al. | 426/425 |
| 4,472,442 | 9/1984 | Katz | 426/428 |
| 4,493,854 | 1/1985 | Friedrich et al. | 426/425 |
| 4,548,755 | 10/1985 | Stahl et al. | 260/412.8 |
| 4,601,906 | 7/1986 | Shindler | 426/425 |
| 4,632,837 | 12/1986 | Schutz et al. | 426/425 |
| 4,703,060 | 10/1987 | Traitler et al. | 514/549 |
| 4,714,526 | 12/1987 | Pennisi et al. | 203/49 |

Primary Examiner—Curtis R. Davis
Assistant Examiner—William C. Diemler
Attorney, Agent, or Firm—Thomas Zack; Alvin J. Englert; Holly D. Kozlowski

[57] ABSTRACT

A method and apparatus for the separation of a desired product from a supercritical fluid extraction solution employ a restrictor nozzle, a coarse-pore sintered-glass enclosure member and a collecting means for collecting an oil suspension of the desired product. The supercritical fluid extraction solution is decompressed by passing through the restrictor nozzle. The resulting decompressed fluid stream is directed at the enclosure member which is saturated with an oil in which the desired product is soluble. Solutes including the desired product are dissolved in the oil, and the oil is collected. The method and apparatus are particularly suitable for use in separating $\beta$-carotene from a carbon dioxide solvent.

20 Claims, 2 Drawing Sheets

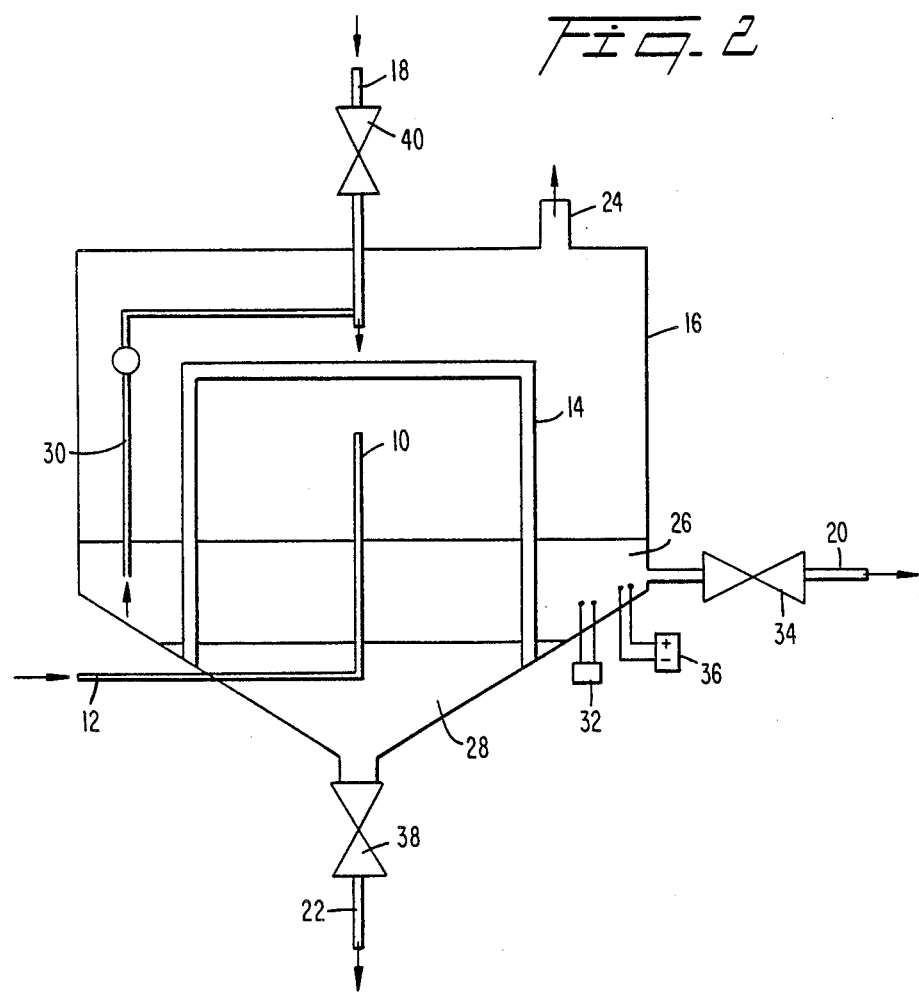

METHOD AND APPARATUS FOR SUPERCRITICAL FLUID EXTRACTION SOLUTION SEPARATION

FIELD OF THE INVENTION

The present invention relates to a method and apparatus for the separation of a desired product from a supercritical fluid extraction solution. The method and apparatus are particularly suitable for use in separating natural products such as $\beta$-carotene from supercritical fluid extraction solutions.

BACKGROUND OF THE INVENTION

Many important natural products are high value-added commodities which are produced industrially on relatively small scale. For example, $\beta$-carotene is produced at a level of approximately 45,000 kg per year, generating between 80 and 100 million dollars in annual sales. There are many important applications of $\beta$-carotene, the most significant of which is its action as the most potent vitamin A precursor in the human body. In this respect, it is employed extensively as a nutritional supplement. $\beta$-carotene is also employed as a safe food and drug colorant, and has therapeutic uses in the treatment of several skin disorders. Most of the worldwide production of $\beta$-carotene is by synthetic means, although carotenoids are produced in nature at a level of approximately $10^8$ tons per year by plants and vegetables.

The high cost of synthetic $\beta$-carotene and the relative abundance of natural $\beta$-carotene makes $\beta$-carotene an ideal candidate for supercritical fluid extraction from natural sources. The use of natural products extracted using nontoxic solvents such as supercritical carbon dioxide has become very attractive during the last decade. The extraction of caffeine from coffee is an example of a successful application of this technology on an industrial scale.

While there have been many laboratory successes in supercritical extraction, scale-up to the commercial level has been slow for a variety of reasons. The control of the extraction process, which depends on solvent-solute phase equilibrium, is extremely difficult. Favorable designs often require operation in tightly constrained regions of the phase diagram. In addition, the natural product solutes of interest, such as $\beta$-carotene, can be very unstable and are subject to degradation by light, heat and oxidation.

One economical process design, based on minimum utility cost and minimum annualized cost, which has been developed for extraction of $\beta$-carotene using supercritical carbon dioxide is depicted schematically in FIG. 1. One serious shortcoming of this process concerns the separator which comprises a simple flash tank. First, the residence time in the flash tank is very high and can lead to chemical decomposition of the extracted $\beta$-carotene. Second, the product can contain up to 20 percent water, whereby an additional drying step, which may make the entire process uneconomical, is required. Third, even if the drying process may be done economically, the resulting $\beta$-carotene powder is itself very unstable, and must be cooled to $-40°$ C. for storage. These problems are encountered in the supercritical extraction of many other natural products as well since many such compounds have similar instabilities. An additional disadvantage is encountered in the flash tank separator employed in the method of FIG. 1. Since the product is a solid, the separator shown in FIG. 1 cannot operate in a true continuous mode, and the product must be removed from the separator in a semi-batch mode using lock-hopper techniques.

Additional extraction methods employing carbon dioxide under supercritical conditions are disclosed in the Schwengers U.S. Pat. No. 3,939,281, the Schultz U.S. Pat. No. 3,966,981 and the Schutz et al U.S. Pat. No. 4,632,837. The methods disclosed in these references generally teach that the extracted products are precipitated as liquids and the low boiling carbon dioxide solvent is converted to the gaseous state and recycled for further extraction use. The Vitzthum et al U.S. Pat. Nos. 4,123,559 and 4,198,432 disclose processes for the production of spice extracts by extraction with a supercritical gas such as carbon dioxide. The essential oils are withdrawn by treating the spices with dry, supercritical carbon dioxide while the flavor components are withdrawn by treating the spices with wet, supercritical carbon dioxide. Additional supercritical and related extraction methods are disclosed in the Laws et al U.S. Pat. Nos. 4,212,895 and 4,218,491, the Shimshick U.S. Pat. No. 4,250,331, the Wheldon et al U.S. Pat. No. 4,282,259, the Katz U.S. Pat. No. 4,472,442, the Friedrich et al U.S. Pat. No. 4,493,854, the Stahl et al U.S. Pat. No. 4,548,755, the Shindler U.S. Pat. No. 4,601,906, the Traitler et al U.S. Pat. No. 4,703,060 and the Pennisi et al U.S. Pat. No. 4,714,526. However, none of these cited references provide a teaching which overcomes the disadvantages noted above encountered in the separation of desired natural products such as $\beta$-carotene from the supercritical fluid extraction solution.

SUMMARY OF THE INVENTION

Accordingly, it is an object of the present invention to provide an improved method and apparatus for the separation of a desired product from a supercritical fluid extraction solution. It is a further object of the invention to provide a method and apparatus for the separation of desired natural products from supercritical fluid extraction solutions which overcome the disadvantages of the prior art and which may be economically employed. It is a further object of the invention to provide such a method and apparatus which provide a product which is in a stable form and suitable for commercial use without further extensive processing. It is an additional object of the invention to provide such a method and apparatus which may be operated in a true continuous mode to provide the desired product.

These and additional objects and advantages are provided by the method and apparatus of the present invention. The present invention provides for the separation of a desired product from a supercritical fluid extraction solution. The method and apparatus employ a restrictor nozzle, a coarse-pore sintered-glass enclosure member and a collecting means for collecting an oil suspension of the desired product. First, the supercritical fluid extraction solution is decompressed by passing the solution through the restrictor nozzle. The resulting decompressed fluid stream is then directed at the enclosure member which is saturated with an oil in which the desired product is soluble. This causes the gaseous solvent to escape through the coarse pores of the enclosure member while the solutes including the desired product are entrained and dissolved in the oil. The oil containing the desired product is then collected whereby the desired product is in a stabilized form suitable for commercial use. The method and apparatus are particularly suitable for use in separating natural products from supercritical solvents, for example in separating β-carotene from a supercritical carbon dioxide solvent.

These and additional objects and advantages will be more fully apparent in view of the following detailed description.

BRIEF DESCRIPTION OF THE DRAWING

The following detailed description will be more fully understood in view of the drawing in which:

FIG. 2 is a schematic diagram of one embodiment of the apparatus according to the present invention.

DETAILED DESCRIPTION

Figure 1:
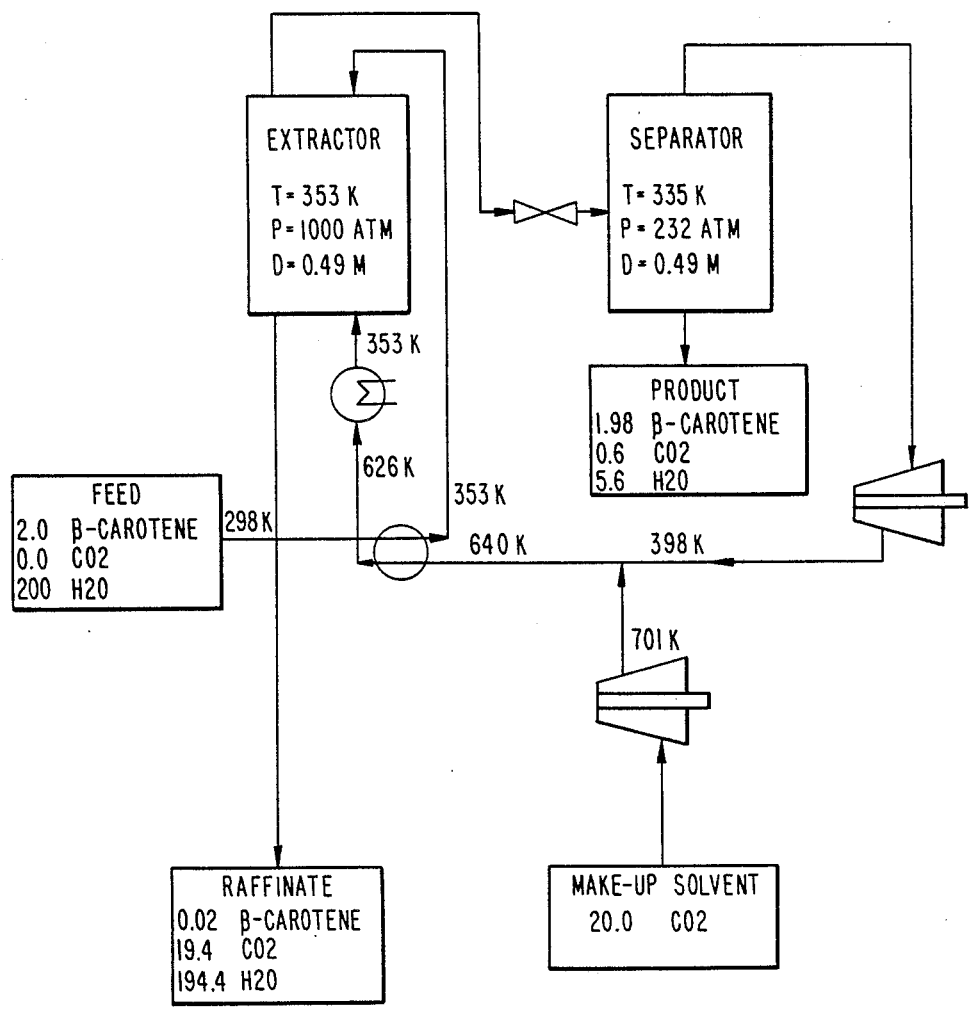
FIG. 1 represents a schematic diagram of a known process for the supercritical fluid extraction of β-carotene using carbon dioxide as a supercritical fluid extractant.

The method and apparatus of the present invention are suitable for use in the separation of a desired product from a supercritical fluid extraction solution. The method and apparatus are particularly suitable for use in the separation of natural products from such extraction solutions. While the present invention will be described with specific reference to the separation of β-carotene from a supercritical fluid extraction solution including a carbon dioxide solvent, the present method and apparatus are equally suitable for use in the separation of other natural products from supercritical fluid extraction solutions.

According to the present method, the supercritical fluid extraction solution resulting from the extraction process, for example an extraction process as described in FIG. 1, is first decompressed by passing the solution through a restrictor nozzle. As the decompression occurs, one or more solutes including the desired product, for example β-carotene, will separate out of solution and the supercritical solvent, for example carbon dioxide, will change to its gaseous state. The resulting fluid stream of solute and gaseous solvent is directed at a coarse-pore sintered-glass or sintered metal enclosure member which is saturated with an oil in which the desired product is soluble. The gaseous solvent escapes through the coarse pores of the enclosure member while the one or more solutes including the desired product are entrained and dissolved in the oil which saturates the enclosure member. As the enclosure member is maintained in a saturated state, oil containing the desired product therein will collect, for example by gravity at the lower portion of the enclosure member, and form an oil layer.

It is well known that oil solutions of many natural products are stable. For example, β-carotene in an oil solution, particularly cottonseed oil, is very stable as long as light is excluded. Approximately 30 percent of β-carotene supplied to the marketplace is in this form. Thus, the present method and apparatus provide a product which is suitable for commercial use.

As noted above, FIG. 1 discloses a known process for the supercritical fluid extraction of β-carotene using carbon dioxide as the supercritical fluid extractant. The composition of a typical extract from the extractor shown in FIG. 1 comprises 1.98 parts β-carotene, 781.2 parts carbon dioxide and 13.7 parts water. This extract is suitable for use as the supercritical fluid extraction solution in the present method and apparatus.

The temperature and pressure employed in the present method and apparatus are generally controlled in order to minimize any oil uptake by the decompressed solvent. The temperature and pressure may be controlled at elevated levels in order to achieve this purpose. Alteratively, the method and apparatus may employ both ambient temperature and pressure (250° C. and 1 atmosphere) since the dissolution ability of solvents such as carbon dioxide drops quickly with decreasing pressure. Thus, the method and apparatus according to the present invention exhibit a significant advantage over the separator shown schematically in FIG. 1 which operates at a temperature of 335 K (62° C.) and 232 atm. The present method and apparatus are also advantageous over the separator shown in FIG. 1 in that the product provided by the present method and apparatus, namely an oil suspension of the desired product, is suitable for commercial use while the product resulting from the separator shown in FIG. 1 consisting of a simple flash tank produces a solid product which may require drying and may be inherently unstable.

Various oils are suitable for use in the present method and apparatus. An important feature is that the desired product is soluble in the oil. It is also desirable that the desired product is stable in the oil. When the desired product of separation comprises β-carotene, a particularly suitable oil for use in the present method and apparatus comprises cottonseed oil. Cottonseed oil is available commercially from various sources.

An embodiment of an apparatus according to the present invention is set forth in FIG. 2. The separation apparatus of FIG. 2 includes a restrictor nozzle 10 through which the supercritical fluid extraction solution passes and which causes decompression of the solution. The supercritical fluid extraction solution is supplied to the restrictor nozzle from an extractor via line 12. The separation apparatus of FIG. 2 further includes an enclosure member 14 formed of a coarse-pore sintered-glass material. The pores of the enclosure member 14 are sufficiently large to allow passage of the gaseous solvent which results from decompression of the extraction solution. The enclosure member may be of any shape which surrounds the outlet of the restrictor nozzle. The apparatus of the invention also includes collecting means for collecting an oil suspension of the desired product. In the apparatus of FIG. 2, the collection means comprises the lower portion of the separation vessel 16 in which the restrictor nozzle and the enclosure member are arranged.

With further reference to FIG. 2, the apparatus of the invention preferably includes an oil inlet 18 for supplying oil to the enclosure member, an oil suspension outlet 20 for removing the oil containing the desired product from the separation vessel and a water outlet 22 for removing carryover water which is also contained in the extraction solution and is separated therefrom. A solvent outlet 24 is also provided in the separation vessel through which the gaseous solvent from the extraction solution is removed. The solvent which exits from outlet 24 may suitably be recycled to the extractor as in the method shown schematically in FIG. 1, if desired.

During steady state operation of the separation apparatus, a supercritical fluid extraction solution is directed via line 12 to the restrictor nozzle 10 where it is decompressed and the resulting fluid stream is directed at the enclosure member 14. Gaseous solvent travels through the porous enclosure member and exits the separation vessel via outlet 24 while one or more solutes including the desired product are entrained and solubilized in oil which saturates the enclosure member 14. Oil containing the desired product is collected as an oil layer 26 while carryover water originally contained in the extraction solution and separated therefrom during the decompression operation collects in a water layer 28. Prior to steady state operations, oil from the oil layer may be recirculated to the enclosure member via recycle line 30.

In a preferred embodiment, means are provided for continuously monitoring the concentration of the desired product and the moisture content in the collected oil suspension, and for activating the oil suspension outlet and the water outlet valves, respectively, in response to detected values. For example, a continuous monitoring means 32, for example an ultraviolet-visible sensor and spectrophotometer, may be employed for continuously monitoring the concentration of the desired product in the collected oil suspension. The detected concentration may then be employed in a means for actuating an oil suspension outlet valve 34. That is, when a predetermined concentration of the desired product is detected in the collected oil suspension, the oil suspension outlet valve 34 is opened to allow removal of the oil suspension product. Similarly, a monitoring means, for example a conductivity sensor and measuring means 36, may be included for monitoring the moisture content of the collected oil suspension, and the detected value may be employed in a means for actuating the water outlet valve 38. That is, when a predetermined moisture content is detecred in the collected oil suspension, the water outlet valve 38 is opened to allow removal of excess water from the water layer formed in the separation apparatus. The water which is removed from collected layer 28 may be treated as necessary in order to comply with environmental regulations.

Prior to steady state operation of the apparatus according to the invention, the concentration of the desired product in the oil layer 26 will be low. The concentration of the desired product will increase as the oil is recirculated via line 30 over the porous enclosure member. When the concentration of the desired product reaches the predetermined value, valve 34 will be automatically adjusted to allow the oil suspension containing the desired product to be removed. Thus, the present method and apparatus result in a market-quality and market-concentration product while operating in a true continuous mode. The monitoring means which monitors the concentration of desired product in the collected oil suspension may also be used to control operation of an oil inlet valve 40 for replenishing the oil phase which is removed.

The method and apparatus of the invention are demonstrated by the following example.

EXAMPLE

An apparatus as shown in FIG. 2 was constructed and operated on a laboratory scale under manual control. The external separation vessel was made of Pyrex glass while the enclosure member comprised a fibrous thimble. All transfer lines were 316 stainless steel tubing. The restrictor nozzle comprised a 0.007 inch inside diameter tube in which a 0.005 inch diameter wire was inserted. The concentration of the collected oil product was monitored using a commercial diode array ultraviolet-visible spectrophotometer set to monitor 450 nm, the absorption maximum for $\beta$-carotene. Cottonseed oil obtained from a chemical supplier without further purification was used to saturate the enclosure member. The prototype device was operated at 22° C. and at ambient pressure. A simulated supercritical fluid extraction solution of carbon dioxide was obtained from a supercritical fluid chromatograph using a sample preparation device charged with $\beta$-carotene. The separation apparatus was able to collect the $\beta$-carotene emerging from the restrictor in the oil. The oil containing the $\beta$-carotene was then collected. The characteristic odor of $\beta$-carotene which was discernible as the simulated extraction solution exited the chromatograph could not be detected after the extraction solution was passed through the separation apparatus. Additionally, there was no other evidence of any undissolved $\beta$-carotene product. The collected oil was colored with the $\beta$-carotene solute which was detected using the ultraviolet-visible spectrophotometer.

This example is set forth to illustrate a specific embodiment of the invention and is not intended to limit the scope of the method and apparatus of the present invention. Additional embodiments and advantages within the scope of the claimed invention will be apparent to one of ordinary skill in the art.

What is claimed is:

1. An apparatus for the separation of a desired product from a supercritical fluid extraction solution, comprising
   (a) a restrictor nozzle through which the supercritical fluid extraction solution passes and which causes decompression of the solution;
   (b) a coarse-pore sintered-glass or sintered metal enclosure member surrounding the restrictor nozzle and at which the decompressed fluid stream is directed, the coarse-pore sintered-glass enclosure member being saturated with an oil; and
   (c) collecting means for collecting an oil suspension of a desired product.

2. An apparatus as defined by claim 1, further including a separation vessel in which the restrictor nozzle, the enclosure member and the collecting means are arranged.

3. An apparatus as defined by claim 2, further including an oil inlet for supplying oil to the enclosure member, an oil suspension outlet, and a water outlet.

4. An apparatus as defined by claim 3, further including means for continuously monitoring the concentration of a desired product in the collected oil suspension and means for activating the oil suspension outlet when a predetermined concentration of desired product is detected in the collected oil suspension.

5. An apparatus as defined by claim 4, wherein the continuous concentration monitoring means comprises an ultraviolet-visible sensor and spectrophotometer.

6. An apparatus as defined by claim 3, further including means for monitoring the moisture content of the collected oil suspension and means for actuating the water outlet when a predetermined moisture content is detected in the collected oil suspension.

7. An apparatus as defined by claim 6, wherein the moisture content monitoring means comprises conductivity sensor and measuring means.

8. An apparatus as defined by claim 2, wherein the separation vessel includes a gas outlet for gaseous components of the decompressed solution which pass through the coarse-pore enclosure member.

9. A method for the separation of a desired product from a supercritical fluid extraction solution, comprising (a) decompressing the supercritical fluid extraction solution by passing it through a restrictor nozzle;

(b) directing the decompressed fluid stream at a coarse-pore sintered-glass or sintered metal enclosure member which is saturated with a oil in which the desired product is soluble, causing gaseous solvent to escape through the coarse pores of the enclosure member and at least one solute comprising the desired product to dissolve in the oil; and (c) collecting the oil containing the desired product.

10. A method as defined by claim 9, wherein the oil containing the desired product is collected in a separation vessel 11. A method as defined by claim 10, further including continuously monitoring the concentration of the desired product in the collected oil and removing oil containing the desired product from the separation vessel once a predetermined concentration of desired product is detected in the collected oil.

12. A method as defined by claim 11, wnerein the concentration of desired product is monitored by an ultraviolet-visible spectrophotometer.

13. A method as defined by claim 10, wherein carryover water from the supercritical fluid extraction solution is collected in a water layer located under a layer of the collected oil.

14. A method as defined by claim 10, further including monitoring the moisture content of the collected oil and removing collected water from the separation vessel once a predetermined moisture content is detected in the collected oil.

15. A method as defined by claim 14, wherein the moisture content is monitored by a conductivity measuring means.

16. A method as defined by claim 9, wherein the desired product comprises $\beta$-carotene.

17. A method as defined by claim 16, wherein the supercritical fluid extraction solution comprises $\beta$-carotene in carbon dioxide.

18. A method as defined by claim 16, wherein the oil comprises cottonseed oil.

19. A method as defined by claim 9, wherein the method is conducted at ambient pressure and temperature.

20. A method as defined by claim 9, wherein the method is conducted at an elevated temperature and pressure.

* * * * *